(12) United States Patent
Oka et al.

(10) Patent No.: US 8,257,916 B2
(45) Date of Patent: Sep. 4, 2012

(54) METHOD FOR DETECTING INTEGRATED HPV DNA

(75) Inventors: Noriko Oka, Kobe (JP); Masahiro Kajita, Kobe (JP); Hideki Ishihara, Miki (JP)

(73) Assignee: Sysmex Corporation, Hyogo (JP)

( * ) Notice: Subject to any disclaimer, the term of this patent is extended or adjusted under 35 U.S.C. 154(b) by 525 days.

(21) Appl. No.: 12/262,508

(22) Filed: Oct. 31, 2008

(65) Prior Publication Data

US 2009/0111090 A1    Apr. 30, 2009

(30) Foreign Application Priority Data

Oct. 31, 2007  (JP) ................................ 2007-283502
Mar. 28, 2008  (JP) ................................ 2008-087682

(51) Int. Cl.
*C12Q 1/70* (2006.01)
*C12P 19/34* (2006.01)

(52) U.S. Cl. ........ 435/5; 424/204.1; 435/6.12; 435/91.2

(58) Field of Classification Search .................. None
See application file for complete search history.

(56) References Cited

U.S. PATENT DOCUMENTS 5,968,522 A * 10/1999 Orth et al. ................... 424/204.1
6,083,692 A *  7/2000 Satishchandran et al. ........ 435/6

OTHER PUBLICATIONS

Peitsaro et al. (Journal of Clinical Microbiology, 2002, vol. 40, p. 886-891).*
Ha et al. (Clinical Cancer Research, 2002, vol. 8, p. 1203-1209).*
Tsunehiro Mukai, et al., "Isolation of Circular DNA Molecules from Whole Cellular DNA by Use of ATP-Dependent Deoxyribonuclease", Proc. Nat. Acad. Sci. USA, Oct. 1973, pp. 2884-2887, vol. 70, No. 10.
Panu Peitsaro, et al., "Integrated Human Papillomavirus Type 16 Is Frequently Found in Cervical Cancer Precursors as Demonstrated by a Novel Quantitative Real-Time PCR Technique", Journal of Clinical Microbiology, Mar. 2002, pp. 886-891, vol. 40, No. 3.
Hugo Arias-Pulido, et al., "Human Papillomavirus Type 16 Integration in Cervical Carcinoma in Situ and in Invasive Cervical Cancer", Journal of Clinical Microbiology, May 2006, pp. 1755-1762, vol. 44, No. 5.
Renske D. M. Steenbergen, et al., "Integrated Human Papillomavirus Type 16 and Loss of Heterozygosity at 11q22 and 18q21 in an Oral Carcinoma and Its Derivative Cell Line", Cancer Research, Nov. 1995, pp. 5465-5471, vol. 55.

* cited by examiner

*Primary Examiner* — Agnieszka Boesen
(74) *Attorney, Agent, or Firm* — Sughrue Mion, PLLC

(57) ABSTRACT

A method for detecting integrated HPV DNA is described herein. This method comprises obtaining first and second samples, obtaining first and second information, and detecting, based on the first and second information, the HPV DNA integrated into the genome of a cell derived from a subject. The second sample comprises DNA derived from the cell, which is treated with an enzyme having exonuclease activity. The first information is related to the amount of HPV DNA in the first sample, and the second information is related to the amount of HPV DNA in the second sample.

16 Claims, 5 Drawing Sheets

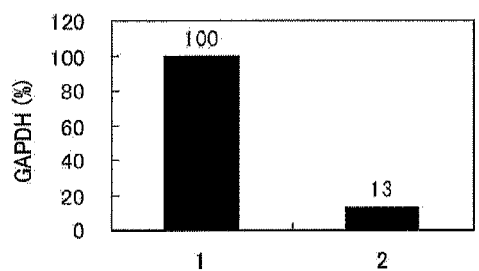
Fig.7(A)
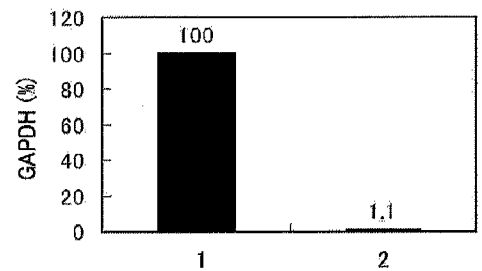
Fig.7(B)
Fig. 8
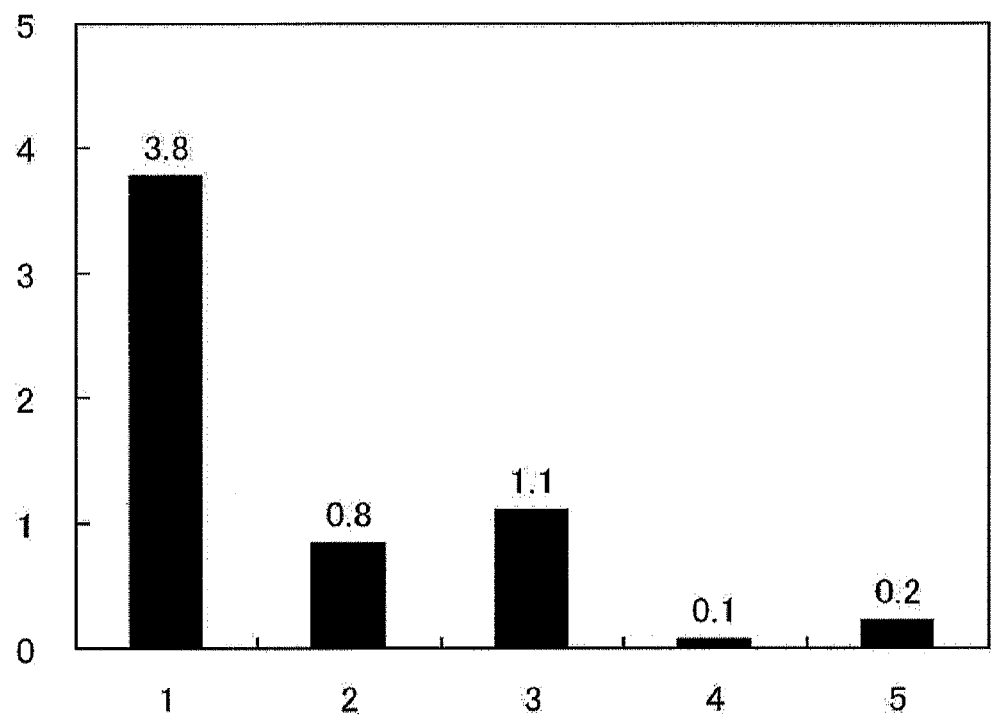

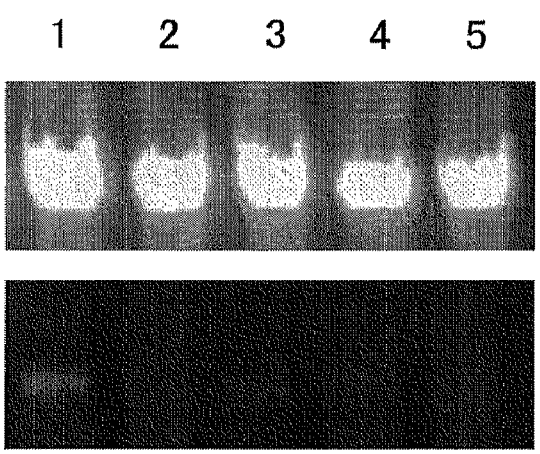

METHOD FOR DETECTING INTEGRATED HPV DNA

TECHNICAL FIELD

The present invention relates to a method for detecting integrated HPV DNA.

BACKGROUND

Human papillomavirus (hereinafter referred to as "HPV") is a virus that causes a papilloma. HPV is classified into 100 or more subtypes. Among the HPV subtypes, common gene regions are known to be preserved. HPV (integrated HPV) integrated in genomic DNA, and HPV (episomal HPV) in the state of a double-stranded circular DNA, occur in cells infected with HPV. It is known that HPV occurs often as integrated HPV in cancer tissues such as tissues of cervical intraepithelial neoplasia occurring the uterine cervix and tissues of oral cancer. Accordingly, the detection of integrated HPV in a cell collected from a subject is important in examining the cancerous state of the cell.

Peitsaro et al. (Journal of Clinical Microbiology, 40, pp. 886-891 (2002)) and Arias-Pulido et al. (Journal of Clinical Microbiology, 44, pp. 1755-1762 (2006)) describe methods of judging the integration of HPV16 in the genomic DNA of a cell with a quantitative real time PCR. Specifically, the DNA amount of an E2 gene region of HPV16 and the DNA amount of an E6 gene region of HPV16 are first measured and their measurements are compared. On the basis of the comparison result, the integration of HPV16 DNA in the genomic DNA of a cell is then judged. The E2 gene region is a region that is often cleaved due to the integration of HPV16 DNA in the genomic DNA. According to the methods described in Peitsaro et al. and Arias-Pulido et al., the presence or absence of the integration of HPV16 in the genomic DNA can therefore be judged on the basis of a variation in the amount of the DNA in the E2 gene region.

However, there is a case where in integration of HPV16 in the genomic DNA, HPV16 DNA is not cleaved in the E2 gene region. Accordingly, even if HPV16 DNA has been integrated in the genomic DNA of a cell, the variation in the amount of the DNA, caused by cleavage of the E2 gene region, may not occur. Accordingly, the methods described by Peitsaro et al. and Arias-Pulido et al. are not accurate enough to detect the integration of HPV16 DNA in the genomic DNA of the host cell.

Steenbergen et al. (Cancer Research, 55, pp. 5465-5471 (1995)) describe a method of detecting the integration of HPV16 DNA in the genomic DNA by fluorescent in situ hybridization (FISH).

However, FISH is complex in operation and requires skills. Accordingly, the integration of HPV DNA in the genomic DNA cannot be easily detected.

SUMMARY

The object of the present invention is to provide a method for detecting an integrated HPV easily with high accuracy.

The method for detecting integrated HPV DNA according to the present invention comprises obtaining first and second samples, first and second information, and detecting the HPV DNA integrated into the genome of a cell derived from a subject based on the first and second information. The first sample comprises DNA which is derived from the cell. The second sample comprises DNA which is derived from the cell and treated with enzyme having exonuclease activity. The first information is related to the amount of HPV DNA in the first sample and the second information is related to the amount of HPV DNA in the second sample.

The method for determining the presence or absence of integrated HPV DNA according to the present invention comprises obtaining the first and second samples, obtaining the first and second information, and determining the presence or absence of the integrated HPV DNA in the cell based on the first and second information.

BRIEF DESCRIPTION OF THE DRAWINGS

FIG. 7(A) and FIG. 7(B) show the measurement result of realtime PCR in the Examination 1. Bar 1 and Bar2 of FIG. 7(A) and Bar 1 and Bar2 of FIG. 7(B) show measurements result of Comparative example 1, Example 5, Comparative example 2, and Example 6, respectively.

FIG. 8 shows the measurement result of realtime PCR in the Examination 2.

FIGS. 9(A) and 9(B) show the result of electrophoresis in the Experiment 1.

FIG. 9(A) shows an electrophoresis pattern in the enzyme reaction for 0 hour, and FIG. 9(B) shows an electrophoresis pattern in the enzyme reaction for 7 hours.

DESCRIPTION OF THE PREFERRED EMBODIMENTS

The method for detecting an integrated HPV DNA according to this embodiment comprises the following steps:
obtaining a first sample and a second sample;
obtaining first information and second information; and
detecting an HPV DNA integrated in the genome of a cell derived from a subject.

The first sample is a sample wherein DNA extracted from a cell of a subject is contained. The second sample is a sample wherein DNA extracted from a cell of the subject has been treated with an enzyme having an exonuclease activity (hereinafter referred to as an exonuclease). That is, the operation of isolating an episomal HPV DNA and an integrated HPV DNA from each other, as in the conventional methods, is not necessary in preparing the first and second samples. This contributes to rapid and easy detection of integrated HPV DNA.

In this specification, the episomal HPV DNA refers to HPV DNA not being integrated in the genomic DNA of a cell. The episomal HPV DNA is double-stranded and circular. The integrated HPV DNA refers to HPV DNA integrated in the genomic DNA of a cell.

Figure 1:
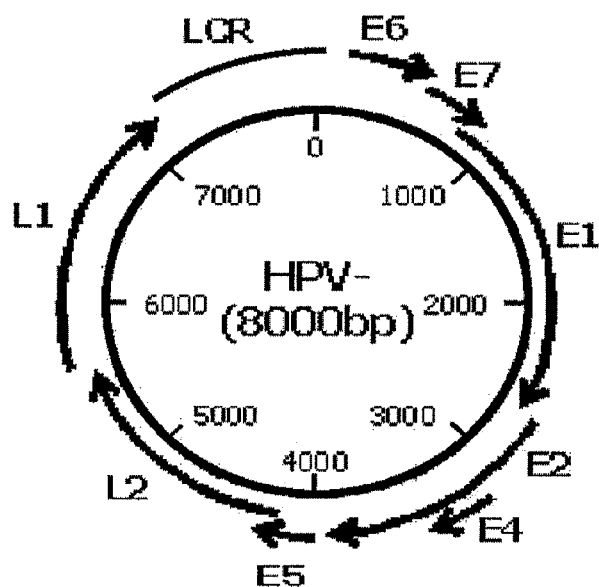
FIG. 1 is a diagrammatic illustration of HPC genome structure.
Figure 2:
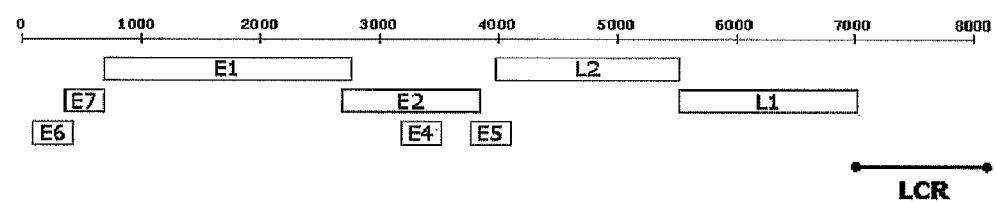
FIG. 2 is a diagrammatic illustration of HPC genome structure.

HPV has an about 8-kb circular DNA. The HPV genome has an early-gene open reading frame (E1 gene region, E2 gene region, E4 gene region, E5 gene region, E6 gene region and E7 gene region), a late-gene open reading frame (L1 gene region and L2 gene region) and an LCR (long control region) (see FIGS. 1 and 2).

The E1 gene region is involved in replication of the viral genome. The E2 gene region is involved in control of viral transcription. The E5 gene region, E6 gene region and E7 gene region are involved in canceration of a host cell. The E6 gene region encodes a protein binding to a tumor-suppressor protein p53 and promoting decomposition of p53. The E7 gene region encodes a protein binding a tumor-suppressor protein Rb and inactivating Rb. The L1 gene region and L2 gene region are involved in encapsidation. The LCR is involved in regulation of viral gene expression.

Among the gene regions mentioned above, the E6 gene region, E7 gene region, L1 gene region and L2 gene region are hardly cleaved on the occasion of integration in the genome of a host cell. That is, when the circular HPV genome is integrated in the genome of a host cell, the circular HPV genome often becomes linear by cleavage of a region other than these gene regions. Particularly, the E6 gene region and E7 gene region are regions with extremely low frequency of cleavage. Therefore, preferably these genes become targets to detect integrated HPC DNA.

The DNA to be detected in this embodiment is preferably a DNA of high risk type HPV. The high risk type HPV is a HPV that is likely to make a cell cancerous by integration in the genomic DNA of the cell. Examples of such high risk type HPV which is at present known by skilled person include HPV16, HPV18, HPV31, HPV33, HPV35, HPV39, HPV45, HPV51, HPV52, HPV56, HPV58, HPV59, HPV68, HPV73, and HPV82.

In the method for detecting an integrated HPV according to this embodiment, a first sample containing DNA derived from a cell of a subject is first obtained.

Obtaining DNA from a cell of a subject may be conducted by a method known in the art. For example, a DNA extraction method such as phenol extraction or phenol-chloroform extraction can be used. Alternatively, a commercial DNA extraction kit may be used.

The extracted DNA can be contained in water or a buffer to form a DNA solution. This DNA solution can be dispensed to prepare first and second samples. Examples of water or a buffer for containing the extracted DNA include nuclease-free PCR-grade water, TE buffer (containing 10 mM Tris-HCl buffer, pH 8.0, 1 mM EDTA), and the like. The DNA may be obtained in preparation of each of the first and second samples.

The first sample contains DNA derived from a cell of a subject. The first sample, unlike the second sample as described later, is not treated with an enzyme having an exonuclease activity. However, the first sample is preferably prepared under the same conditions as for the second sample except for the enzyme treatment. The reliability of judgment in this embodiment can thereby be improved.

The cell of a subject may be any cell to be infected with HPV. Examples of the cell include mucosa cells, skin cells, and the like. The mucosa includes, for example, lumen surfaces of hollow organs such as genitourinary organs, digestive organs and respiratory organs. Specific examples include mucosa cells in uterine cervix and oropharynx. In the method in this embodiment, the cell of a subject is preferably a cell of uterine cervix or a cell of oropharynx.

Then, the DNA derived from a cell of a subject is treated with an exonuclease to obtain a second sample. The second sample contains the exonuclease-treated DNA derived from the subject.

By exonuclease treatment, a linear genomic DNA is decomposed, while a circular DNA is not substantially decomposed. Accordingly, the second sample does not substantially contain HPV DNA integrated in the genomic DNA, but contains the episomal HPV DNA selectively.

In this specification, the enzyme having an exonuclease activity is an enzyme having an activity of hydrolyzing phosphodiester bonds of a linear DNA sequentially from the 5'- to 3'-terminal of the DNA or from the 3'- to 5'-terminal of the DNA. The enzyme preferably has an exonuclease activity on a double-stranded DNA. Specific examples of the enzyme include ATP-dependent deoxyribonuclease, exonuclease III, T7 exonuclease, lambda-exonuclease, T4 DNA polymerase, and Pfu DNA polymerase. Preferable among them are polymerase activity-free enzymes, that is, ATP-dependent deoxyribonuclease, exonuclease III, T7 exonuclease and lambda-exonuclease.

The amount of the exonuclease used in DNA treatment may be appropriately determined depending on the type of the enzyme used and the amount of DNA contained in the first sample. The treatment of DNA with the exonuclease may be carried out under reaction conditions depending on the type of the exonuclease used. From the viewpoint of obtaining the detection result of the integrated HPV DNA with higher accuracy, the treatment of the DNA with the exonuclease is preferably conducted until the DNA is sufficiently digested.

In obtaining the second sample, the DNA obtained from a cell of a subject is treated with the exonuclease and further with an enzyme having an endonuclease activity (referred to hereinafter as an endonuclease) not cleaving the HPV-derived DNA. By endonuclease treatment, the genomic DNA is cut in suitable length, and the DNA cut by the enzyme is decomposed with the exonuclease. Accordingly, the exonuclease treatment can be rapidly conducted to decompose the genomic DNA efficiently. The order in which the exonuclease and endonuclease are added is not particularly limited. Preferably, these enzymes are added simultaneously to the second sample, or the endonuclease is added to the second sample and then the exonuclease is added thereto. Particularly when the endonuclease is added to the second sample and then the exonuclease is added thereto, the endonuclease is preferably inactivated by heating the reaction solution after endonuclease treatment. The cleavage of episomal HPV by the star activity of the remaining endonuclease can thereby be prevented in the subsequent exonuclease treatment. A combination of the endonuclease and the exonuclease is for example a combination of SacI and/or XhoI as the endonuclease and ATP-dependent deoxyribonuclease as the exonuclease.

When the second sample is treated with the endonuclease, the first sample is not treated with the endonuclease.

The endonuclease should be an enzyme whose recognition sequence does not exist in the nucleotide sequence of the HPV genome. For example, when human papillomavirus is HPV16, examples of the endonuclease include ClaI, EcoRV, HindIII, NheI, NotI, SacI, SacII, SalI, SmaI, XbaI, and XhoI. The endonuclease may be used alone or as a mixture of two or more thereof. The amount of the endonuclease used may be suitably determined depending on the type of the enzyme and the amount of the DNA contained in a sample.

In treatment of the DNA, the amount of the endonuclease and the amount of the exonuclease may be appropriately determined depending on the type of the enzyme and the amount of the DNA contained in a sample.

In the method in this embodiment, the first information related to the amount of HPV DNA contained in the first sample and the second information related to the amount of HPV DNA contained in the second sample are obtained.

As described above, the second sample is substantially free of the integrated HPV DNA, and selectively contains the episomal HPV DNA. Accordingly, the second information obtained from the second sample is information on the amount of the episomal HPV DNA. On the other hand, the first sample is not treated with the exonuclease. Accordingly, the first sample contains both the integrated HPV DNA and episomal HPV DNA. Accordingly, the first information obtained from the first sample is information on the amounts of the episomal HPV DNA and integrated HPV DNA.

The information on the amount of HPV DNA contained in a sample refers to information correlated with the quantity (mass) of HPV DNA contained in the sample. For example, in the case of real-time PCR as described later, the information on the amount of HPV DNA includes not only the quantitative value of HPV DNA calculated from a calibration curve but also the amount of the amplification product at a predetermined number of PCR cycles, a number of PCR cycles until the predetermined amount of the amplification product is reached, and a graph of an amplification curve of the amplification product. That is, the information on the amount of HPV DNA contained in a sample includes information that not only directly but also indirectly indicates the amount of the DNA in a sample. The concept "amount" used herein includes mass per unit volume, that is, "concentration".

The first information and second information can be obtained by a known DNA measurement method using a nucleic acid amplification method and a DNA chip. Even if the amount of DNA is low, a method of using a nucleic acid amplification method is desirable because the integrated HPV DNA in a cell can be detected. In this specification, the nucleic acid amplification method refers to a method of using a template DNA and primers to amplify copies of the template DNA.

The DNA chip includes a substrate on which a polynucleotide capable of hybridizing with HPV DNA is immobilized. Measurement using the DNA chip can be carried out by a method known in the art. For example, the measurement can be carried out as follows. First, HPV DNA contained in a sample is used as a template to prepare a biotin-labeled single-stranded DNA probe (biotin-labeled probe). Then, the biotin-labeled probe is contacted with the substrate on which a polynucleotide capable of hybridizing with HPV DNA is immobilized. The biotin-labeled probe and the polynucleotide on the substrate are thereby combined to form a double-stranded chain. The biotin-labeled probe formed into a double-stranded chain with the polynucleotide on the substrate is stained with fluorescently labeled avidin. Thereafter, HPV DNA in the sample can be measured by measuring the fluorescence intensity on the substrate. By this method, HPV DNA contained in the first and second samples can be measured to obtain the first information and second information.

To detect HPV DNA in a sample, a region with low frequency of cleavage in the HPV genome is preferably determined as a detection target. That is, primers used in nucleic acid amplification and probes used in DNA chips are preferably those hybridizing with a region with low frequency of cleavage in the HPV genome. When HPV DNA is integrated in a host cell, one site of the circular HPV genomic DNA is cleaved thereby to make the DNA linear, which is then integrated in the linear genome of a host cell. If a region with high frequency of cleavage is determined as the detection target, it becomes difficult to detect the integrated HPV DNA contained in the first sample.

The region with a low frequency of cleavage is exemplified by the L1 gene region, L2 gene region, L6 gene region and L7 gene region. Among them, the E6 gene region and E7 gene region are regions with very low frequency of cleavage in the integrated HPV DNA sequence.

When the DNA is detected by real-time PCR, it is possible to use the following primer sets:

a primer set of
HPV18L1/LCR-F: 5'-tgctccatctgccactacgtc-3' (SEQ ID NO: 1)
and
HPV18L1/LCR-R: 5'-tagggcgcaaccacataaca-3', (SEQ ID NO: 2)

a primer set of
HPV16E7-F: 5'-tgcatggagatacacctacattg-3' (SEQ ID NO: 3)
and
HPV16E7-R: 5'-tagtgtgcccattaacaggtcttc-3', (SEQ ID NO: 4)

a primer set of
MY09: 5'-cgtccmarrggawactgatc-3' (SEQ ID NO: 5)
and
MY11: 5'-gcmcagggwcataayaatgg-3', (SEQ ID NO: 6)

a primer set of
GP5+: 5'-tttgttactgtggtagatactac-3' (SEQ ID NO: 7)
and
GP6+: 5'-gaaaaataaactgtaaatcatattc-3', (SEQ ID NO: 8)

a primer set of
HPV18E7-F: 5'-caagacattgtattgcatttagagcc-3' (SEQ ID NO: 9)
and
HPV18E7-R: 5'-tgctggaatgctcgaaggtc-3', (SEQ ID NO: 10)

a primer set of
HPV16L1-F: 5'-gtaggtgttgaggtaggtcgtgg-3' (SEQ ID NO: 11)
and
HPV16L1-R: 5'-ggacaatcacctggatttactgc-3', (SEQ ID NO: 12)

a primer set of
HPVpU-1M: 5'-tgtcaaaaaccgttgtgtcc-3' (SEQ ID NO: 13)
and
HPVpU-2R: 5'-gagctgtcgcttaattgctc-3'. (SEQ ID NO: 14)

The DNA is preferably amplified by polymerase chain reaction, strand displacement reaction, or ligase chain reaction. The polymerase chain reaction includes, for example, real-time PCR. The strand displacement reaction includes, for example, LAMP, ICAN (registered trademark), and SMAP. Among them, real-time PCR and LAMP are preferable.

Real-time PCR for detecting and quantifying HPV DNA as an amplification product includes a method of using a fluorescent intercalator (intercalator method) and a method of using a probe (for example, a TaqMan probe, a cycling probe or the like) consisting of a fluorescent dye-labeled oligonucleotide specific for a sequence of an amplification product (probe method). Among them, the intercalator method is preferable from the viewpoint of easy detection and quantification of the amplification product HPV DNA.

In the intercalator method, an intercalator is a substance that binds to a double-stranded DNA synthesized by polymerase chain reaction and emits fluorescence upon irradiation with an exciting light. In the intercalator method, fluorescence intensity based on the fluorescence of the intercalator that is bound to the amplification product and obtained as a double-stranded DNA can be detected to monitor the amount of the amplification product formed. The intercalator includes, for example, SYBR (registered trademark) green manufactured by Molecular Probe Inc.

In real-time PCR, the amplification product is monitored in real time, and on the basis of amplification kinetics in polymerase chain reaction, the HPV DNA can be quantified. As the amount of a template DNA is increased in real-time PCR, a detectable amount of the amplification product is reached at a less number of PCR cycles. The number of cycles (Ct (threshold cycle)) at which a detectable amount of the amplification product is reached is linearly related to the amount of the DNA in the sample. Accordingly, the HPV DNA in a DNA sample can be calculated on the basis of a calibration curve showing the relationship between Ct value and the amount of a standard DNA sample.

In the case of LAMP, magnesium pyrophosphate is formed as a byproduct with the progress of DNA amplification. This magnesium pyrophosphate is insoluble, and thus the reaction solution becomes turbid as magnesium pyrophosphate is increased. Accordingly, the turbidity (or absorbance) of the reaction solution can be measured optically in real time to obtain information on the amount of the DNA in the sample. In LAMP too, SYBR (registered trademark) green manufactured by Molecular Probe Inc. can be used to monitor a change in the fluorescence intensity of the reaction solution in real time, to obtain information on the amount of the DNA. The amount of the HPV DNA in the sample can be calculated on the basis of the time in which the turbidity, absorbance or fluorescence intensity of the reaction solution reaches a predetermined value.

In the method in this embodiment, HPV DNA integrated in the genomic DNA in a cell is detected on the basis of the first information and second information.

As described above, the first information is related to the amount of integrated HPV DNA and the amount of episomal HPV DNA. On the other hand, the second information is related to the amount of episomal HPV DNA. Accordingly, the integrated HPV DNA in a DNA sample extracted from a cell of a subject can be detected by comparing the first information with the second information.

When the amount of HPV DNA contained in the second sample is lower than the amount of HPV DNA contained in the first sample, it can be judged that HPV DNA is integrated in the genomic DNA of the host cell. When HPV DNA contained in the second sample is substantially equal to the amount of HPV DNA in the first sample, it can be judged that HPV DNA is not integrated in the genomic DNA of the host cell.

When the first information and second information are for example on quantitative values of HPV DNA, it can be judged that when the HPV DNA quantitative value according to the second information is lower than the HPV DNA quantitative value according to the first information, the integrated HPV DNA exists in the host cell. On the other hand, it can be judged that when the HPV DNA quantitative value according to the second information is substantially equal to the HPV DNA quantitative value according to the first information, the integrated HPV DNA does not exist in the host cell.

When the first information and second information are on the amount of the amplification product (the amount of HPV DNA amplified) obtained by using the nucleic acid amplification, the amount of the amplification product according to the second information is lower than the amount of the amplification product according to the first information, it can be judged that the integrated HPV DNA exists in the host cell. When the amount of the amplification product according to the second information is substantially equal to the amount of the amplification product according to the first information, it can be judged that the integrated HPV DNA does not exist in the host cell.

If the first information and second information are on the time in which the optical information (turbidity, absorbance, fluorescence intensity or the like) of the reaction solution reaches a predetermined value, it can be judged that when the second time is longer than the first time, the integrated HPV DNA exists in the host cell. It can be judged that when the time according to the second information is substantially equal to the time according to the first information, the integrated HPV DNA does not exist in the host cell. When nucleic aid amplification is conducted by PCR, the number of PCR cycles until the optical information (fluorescence intensity or the like) of the reaction solution reaches a predetermined value can be used as the first information and second information. In this case, it can be judged that when the number of PCR cycles according to the second information is larger than the number of PCR cycles according to the first information, the integrated HPV DNA exists in the host cell. It can be judged that when the number of PCR cycles according to the second information is substantially equal to the number of PCR cycles according to the first information, the integrated HPV DNA does not exist in the host cell.

When the second information is information that HPV DNA does not exist, it can be judged that the episomal HPV does not exist in a cell of the subject. Further, when the first information is also information that HPV DNA does not exist, it can be judged that a cell of the subject is not infected with HPV.

When the second information is information that HPV DNA does not exist and simultaneously the first information is information that HPV DNA exists, it can be judged that every HPV DNA in a cell of the subject is the integrated HPV DNA.

When the amount of HPV DNA in a sample is lower than the limit of detection or when DNA amplification is not confirmed in nucleic acid amplification, it is judged that HPV DNA does not exist in the sample.

On the other hand, when the amount of HPV DNA in a sample is higher than the limit of detection or when DNA amplification is confirmed in nucleic acid amplification, it is judged that HPV DNA exists in the sample.

The information on the presence or absence of HPV DNA is contained in the "information on the amount of HPV DNA" referred to in this specification.

When it is judged that HPV DNA exists in both the first and second samples and simultaneously when it is judged that the amount of HPV DNA in the first sample is larger than the amount of HPV DNA in the second sample, it can be judged that both integrated HPV DNA and episomal HPV DNA exist in a cell of the subject.

In the method in this embodiment, it is preferable that information (third information) on the presence or absence of a control gene in the first sample and/or the second sample is obtained in order to confirm whether the manner to acquire the first sample, the manner to acquire the second sample, and the manner to detect the integrated HPV DNA have been suitably carried out.

The control gene is not particularly limited as long as it exists in the human genome but does not exist in the HPV genome. Examples of the control gene include housekeeping genes (genes for actin, globulin, glyceraldehyde-3-phosphate dehydrogenase (GAPDH), and the like), a ribosomal RNA gene, and the like. Such a gene can be used as the control gene in the control of accuracy in detection of integrated HPV DNA in this embodiment. The housekeeping gene is expressed substantially always at an almost constant level in most kinds of cells in humans, and HPV does not have this gene.

The third information can be obtained by using a DNA detection method known in the art. For example, a nucleic acid amplification reaction is carried out using DNA contained in a sample as a template and primers for detection of a control gene, and from the amplification result, the third information can be obtained.

The genome of a host cell is contained in the first sample, while the genome of the host cell is not contained in the second sample. Accordingly, if the manner to prepare the sample and the manner to acquire information on the amount of DNA have been suitably carried out, the control gene must be detected in the first sample, while the control gene must not be detected in the second sample.

Accordingly, the fact that the control gene is detected in the first sample while the control gene is not detected in the second sample is indicative of high reliability of results in the detection method according to this embodiment.

On the contrary, when the control gene is not detected in the first sample and/or the control gene is detected in the second sample, it can be judged that the manner to prepare the first and second samples and/or the manner to acquire the first and second information was not appropriately carried out.

When the control gene is detected in the first sample and the control gene is also detected in the second sample, there is a possibility that treatment of the second sample with an exonuclease is unsuitable or insufficient.

According to the method of judging the presence or absence of integrated HPV in the present invention, the presence or absence of integrated HPV can be judged rapidly and easily with high accuracy.

Hereinafter, the present invention is described in detail based on Examples, but the present invention is not limited to such Examples.

EXAMPLES

Example 1

The genomic DNA of SiHa cells ($1 \times 10^6$ cells) in an uterine cervix-derived cell strain having HPV16 DNA integrated in the chromosome was extracted with a DNA extraction kit (trade name: QIAamp DNA mini kit, manufactured by QIAGEN). Nuclease-free purified water (PCR grade) was added to the extracted genomic DNA of SiHa cells to give an aqueous solution (0.1 μg/μL) of the genomic DNA of SiHa cells.

The resulting aqueous solution (10 μL) of the genomic DNA of SiHa cells was used to prepare 50 μL buffer containing 1 μg of the genomic DNA of SiHa cells (composition: 66.8 mM glycine-sodium hydroxide (pH 9.4), 30 mM magnesium chloride, 8.4 mM 2-mercaptoethanol, 0.5 m M γATP, 1 μg of the genomic DNA of SiHa cells, and nuclease-free purified water). This buffer was incubated at 37° C. for 2.5 hours and then incubated at 75° C. for 20 minutes to give a first sample (50 μL).

The aqueous solution (10 μL) of the genomic DNA of SiHa cells was used to prepare 50 μL of buffer containing 1 μg of the genomic DNA of SiHa cells and 20 U γATP-dependent deoxyribonuclease (trade name: ATP-Dependent Deoxyribonuclease, code number: ADD-101, manufactured by Toyobo Co., Ltd.) (composition: 66.8 mM glycine-sodium hydroxide (pH 9.4), 30 mM magnesium chloride, 8.4 mM 2-mercaptoethanol, 0.5 mM γATP, 1 μg of the genomic DNA of SiHa cells, 20 U of γATP-dependent deoxyribonuclease, the remaining nuclease-free purified water). The resulting buffer containing the genomic DNA and γATP-dependent deoxyribonuclease was incubated at 37° C. for 2.5 hours. Then, the buffer was incubated at 37° C. for 2.5 hours. Then, the buffer was incubated at 75° C. for 20 minutes to give a second sample (50 μL).

The following materials were mixed to prepare a reaction solution 1 subjected to real-time PCR.
1 μL first sample
9.1 μL water
12.5 μL ×2 Master Mix
0.4 μL Reference Dye
1 μL aqueous solution of primer HPV16E7-F (10 μM, SEQ ID NO: 3:5'-tgcatggagatacacctacattg-3')
1 μL aqueous solution of primer HPV16E7-R (10 μM, SEQ ID NO: 4:5'-tagtgtgcccattaacaggtcttc-3')

"×2 Master Mix" and "Reference Dye" are contained in a real-time PCR kit manufactured by QIAGEN (trade name: Brilliant (registered trademark) SYBR (registered trademark) Green QPCR Master Mix, Catalogue No. #600548).

A primer set consisting of primer HPV16E7-F and primer HPV16E7-R was used for amplifying an E7 gene region of the HPV16 genome.

A reaction solution 2 was prepared in the same manner as for the reaction solution 1 except that the second sample was used in place of the first solution.

Figure 3:
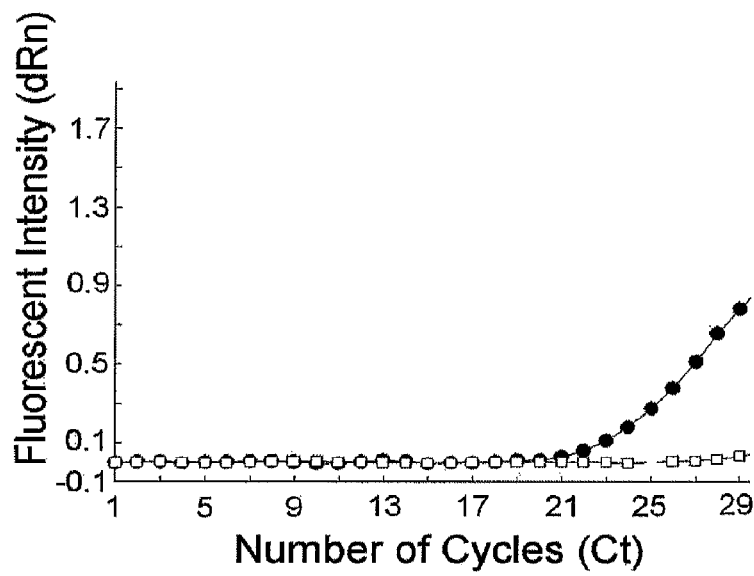
FIG. 3 shows the measurement result of realtime PCR in the Example 1.

Using the reaction solutions 1 and 2 respectively, real-time PCR was conducted by Mx3005P manufactured by STRATAGENE. A thermal profile of the real-time PCR was as follows:
 95° C., 10 minutes,
 30 cycles of 95° C. for 30 seconds, 58° C. for 15 seconds, and 72° C. for 30 seconds In real-time PCR, the fluorescence intensity of a fluorescence dye (trade name: Brilliant (registered trademark) SYBR (registered trademark) Green, manufactured by QIAGEN) intercalated in the double-stranded DNA being an amplification product was measured. The results are shown in FIG. 3. In the graph, the black circles show detection results of the first sample (reaction solution 1), and the rectangles show detection results of the second sample (reaction solution 2).

As shown in FIG. 3, the amount of the amplification product in the reaction solution 1 was increased exponentially after the 20th cycle. On the other hand, the amount of the amplification product in the reaction solution 2 was hardly changed. This is possibly because in the second sample, the genomic DNA of SiHa cells, in which HPV DNA being a linear DNA had been integrated, was decomposed with γATP-dependent deoxyribonuclease.

From the foregoing, it is suggested that when the amount of HPV DNA contained in the second sample is lower than the amount of HPV DNA contained in the first sample, it can be judged that the integrated HPV DNA exists in the cells.

Example 2

An aqueous solution of the genomic DNA of HeLa cells was obtained in the same manner as in Example 1 except that HeLa cells ($1×10^6$ cells) in a cell strain derived from the uterine cervix having HPV18 integrated in the chromosome were used in place of the SiHa cells.

A plasmid wherein HPV DNA in the range of from L1 gene region to E6 gene region of HPV18 genome had been ligated to a vector (trade name: pCEP4 vector, Catalogue No. V044-50, manufactured by Invitrogen) was used as a model of HPV DNA that is a circular double-stranded DNA.

First and second samples were obtained in the same manner as in Example 1 except that an aqueous solution prepared by mixing 1 µg of the genomic DNA of HeLa cells with 500 pg of the plasmid was used in place of an aqueous solution of 1 µg of the genomic DNA of SiHa cells.

Real-time PCR samples (reaction solutions 1 and 2) were prepared in the same manner as in Example 1 except that a primer HPV18L1/LCR-F (SEQ ID NO: 1, 5'-tgctccatctgccactacgtc-3') solution and a primer HPV18L1/LCR-R (SEQ ID NO: 2, 5'-tagggcgcaaccacataaca-3') solution were used in place of the primer HPV16E7-F solution and the primer HPV16E7-R solution. The primer set consisting of primer HPV18L1/LCR-F and primer HPV18L1/LCR-R is a primer set for amplifying the L1 gene region in HPV18.

Figure 4:
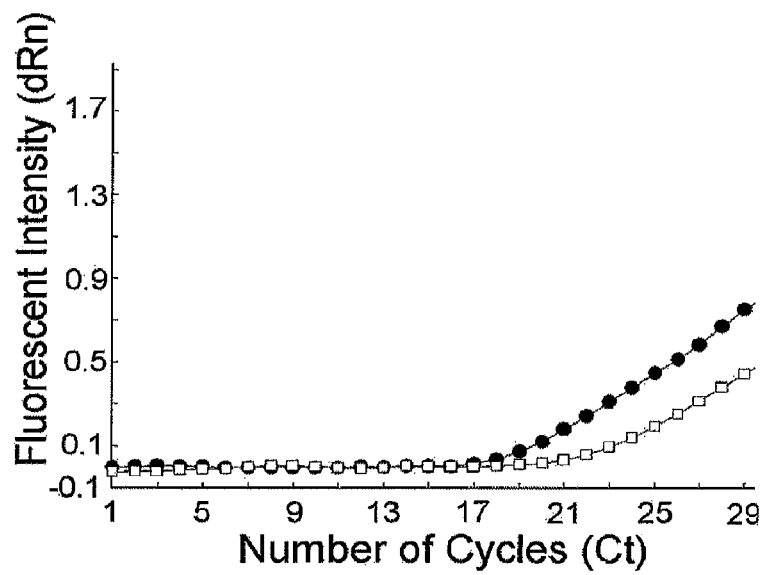
FIG. 4 shows the measurement result of realtime PCR in the Example 2.

Thereafter, real-time PCR was conducted. Its thermal profile is as follows:

95° C., 10 minutes,
30 cycles of 95° C. for 30 seconds, 63° C. for 15 seconds, and 72° C. for 30 seconds The instruments and the like used in real-time PCR are the same as used in Example 1. The measurement results are shown in FIG. 4. In the graph, the black circles show detection results of the first sample (reaction solution 1), and the rectangles show detection results of the second sample (reaction solution 2).

As shown in FIG. 4, the DNA was increased exponentially in both the reaction solutions 1 and 2 after the 18th cycle. Accordingly, it can be known that HPV18 DNA exists in both the first and second samples.

As shown in FIG. 4, the amount of the amplification product in the reaction solution 2 is lower than the amount of the amplification product in the section solution 1 after the 18th cycle, and thus it can be known that HPV18 DNA integrated in the linear genomic DNA does not exist, while the circular double-stranded DNA exists, in the second sample.

Accordingly, it is suggested that when the amount of HPV DNA contained in the second sample is lower than the amount of HPV DNA contained in the first sample, it can be judged that the integrated HPV18 exists in the cell. It is also suggested that the presence or absence of the integrated HPV DNA in the cell can be judged by using, as an indicator, the amount of HPV DNA contained in the first sample.

Example 3

Figure 5:
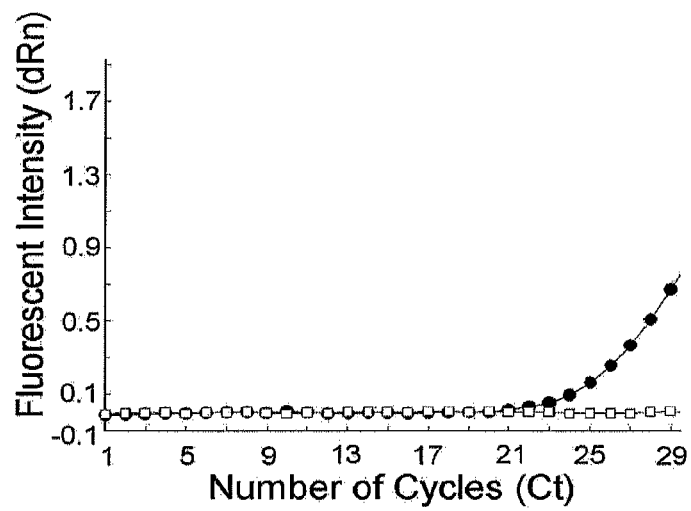
FIG. 5 shows the measurement result of realtime PCR in the Example 3.

A glyceraldehyde-3-phosphate dehydrogenase gene (hereinafter also referred to merely as GAPDH) in the first and second samples in Example 1 was detected by real-time PCR. Real-time PCR was conducted in the same manner as in Example 1 except that a primer set (SEQ ID NO: 15, 5'-ggcaccctatggacacgc-3', and SEQ ID NO: 16, 5'-ggaaagccagtcccca-gaac-3') for amplification of GAPDH was used. The results are shown in FIG. 5. In the graph, the black circles show detection results of the first sample (reaction solution 1), and the rectangles show detection results of the second sample (reaction solution 2).

As shown in FIG. 5, the amount of the amplification product in the reaction solution 1 was increased exponentially after the 21st cycle. Accordingly, it can be known that GAPDH exists in the first sample. As shown in FIG. 5, on the other hand, it can be known that the amount of the amplification product in the reaction solution 1 is hardly changed. From this result, it can be known that in the second sample, an amplification product of GAPDH was not detected because of decomposition of the linear genomic DNA with γATP-dependent deoxyribonuclease. Accordingly, it was found that preparation of the samples, PCR reaction, and nuclease treatment had been properly conducted in Example 1.

As described above, the accuracy of judgment results in Example 1 can be evaluated according to the detection result of the control gene such as GAPDH contained in the first and second samples respectively.

Example 4

Figure 6:
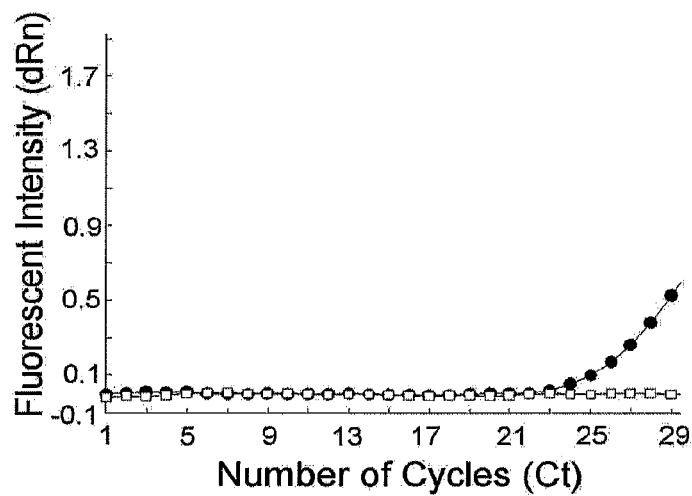
FIG. 6 shows the measurement result of realtime PCR in the Example 4.

The first and second samples in Example 2 were subjected to real-time PCR in the same manner as in Example 2 except that a primer set (SEQ ID NO: 15 and SEQ ID NO: 16) for amplification of GAPDH was used. The results are shown in FIG. 6. In the graph, the black circles show detection results of the first sample (reaction solution 1), and the rectangles show detection results of the second sample (reaction solution 2).

As shown in FIG. 6, the amount of the amplification product in the reaction solution 1 was increased exponentially after the 22nd cycle. Accordingly, it can be known that GAPDH DNA exists in the first sample. As shown in FIG. 6, on the other hand, it can be known that the amount of the amplification product in the reaction solution 2 is hardly changed. From this result, it can be known that in the second sample, GAPDH could not be amplified because of decomposition of the linear genomic DNA with γATP-dependent deoxyribonuclease. Accordingly, it was recognized that the preparation of the samples, PCR reaction, and nuclease treatment had been properly conducted in Example 2.

As described above, the accuracy of judgment results in Example 2 can be evaluated according to the detection result of the control gene such as GAPDH contained in the first and second samples respectively.

Manufacturing Example 1

The genomic DNA of human stomach cancer cell strain KATOIII cells ($1×10^6$ cells) was extracted with a DNA extraction kit (trade name: QIAamp DNA mini kit, manufactured by QIAGEN).

Comparative Example 1

30 µL of buffer containing 5 µg of the genomic DNA of KATOIII cells obtained in Manufacturing Example 1 (composition: 10 mM Tris-HCl (pH 7.5), 10 mM magnesium chloride, 1 mM dithiothreitol, 5 µg of the KATOIII cell genomic DNA, nuclease-free purified water) was prepared. This buffer was incubated at 37° C. overnight. The buffer was further incubated at 60° C. for 15 minutes to give an untreated sample.

To this untreated sample (30 µL) was added 10 µL of γATP-dependent deoxyribonuclease buffer (×5 buffer (composition: 334 mM glycine-sodium hydroxide (pH 9.4), 150 mM magnesium chloride, 42 mM 2-mercaptoethanol, 2.5 mM γATP)). Nuclease-free purified water was added to the resulting mixture to give 50 μL of a reaction mixture. This reaction mixture was incubated at 37° C. for 6 hours and then incubated at 75° C. for 15 minutes. The reaction mixture was purified through a spin column for nucleic acid purification (trade name: MicroSpin S-300 HR Column, manufactured by GE Healthcare) to give the sample in Comparative Example 1.

Example 5

10 μL γATP-dependent deoxyribonuclease buffer (×5 buffer (composition: 334 mM glycine-sodium hydroxide (pH 9.4), 150 mM magnesium chloride, 42 mM 2-mercaptoethanol, 2.5 mM γATP)) and 5U γATP-dependent deoxyribonuclease (trade name: ATP-Dependent Deoxyribonuclease, Code No. ADD-101, manufactured by Toyobo Co., Ltd.) were added to an untreated sample (30 μL) obtained in the same manner as in Comparative Example 1. Nuclease-free purified water was added to the resulting mixture to give 50 μL of a reaction mixture. This reaction mixture was incubated at 37° C. for 6 hours and then incubated at 75° C. for 15 minutes. The reaction mixture was purified through a spin column for nucleic acid purification (trade name: MicroSpin S-300 HR Column, manufactured by GE Healthcare) to give the sample in Example 5.

Comparative Example 2

30 μL buffer containing 5 μg of the genomic DNA of KATOIII cells obtained in Manufacturing Example 1 and 5 U SacI (manufactured by Takara Bio) (composition: 10 mM Tris-HCl (pH7.5), 10 mM magnesium chloride, 1 mM dithiothreitol, 5 μg of the genomic DNA of KATOIII cells, 5 U SacI, nuclease-free purified water). This buffer was incubated at 37° C. overnight. Then, the buffer was incubated at 60° C. for 15 minutes to give an SacI-treated sample.

To the SacI-treated sample (30 μL) was added 10 μL γATP-dependent deoxyribonuclease buffer (×5 buffer (composition: 334 mM glycine-sodium hydroxide (pH 9.4), 150 mM magnesium chloride, 42 mM 2-mercaptoethanol, 2.5 mM γATP)). 10 μL of nuclease-free purified water was added to the resulting mixture to give 50 μL of a reaction mixture. The resulting reaction mixture was incubated at 37° C. for 6 hours and then incubated at 75° C. for 15 minutes. The reaction mixture was purified through a spin column for nucleic acid purification (trade name: MicroSpin S-300 HR Column, manufactured by GE Healthcare) to give the sample in Comparative Example 2.

Example 6

10 μL of the γATP-dependent deoxyribonuclease buffer and 5 U γATP-dependent deoxyribonuclease (trade name: ATP-Dependent Deoxyribonuclease, Code No. ADD-101, manufactured by Toyobo Co., Ltd.) were added to an SacI-treated sample (30 μL) obtained in the same manner as in Comparative Example 2. Nuclease-free purified water was added to the resulting mixture to give 50 μL of a reaction mixture. This reaction mixture was incubated at 37° C. for 6 hours and then incubated at 75° C. for 15 minutes. The reaction mixture was purified through a spin column for nucleic acid purification (trade name: MicroSpin S-300 HR Column, manufactured by GE Healthcare) to give the sample in Example 6.

Examination 1

1 μL of the sample in Example 5 was used to prepare 25 μL of a reaction solution having the following composition:
1 μL of the sample in Example 5,
12.5 μL of ×2 Master Mix
0.4 μL of Reference Dye
1 μL of an aqueous solution of primer GADPH/DNA-F (10 μM, SEQ ID NO: 17:5'-ggcaccctatggacacgc-3')
1 μL of an aqueous solution of primer GADPH/DNA-R (10 μM, SEQ ID NO: 18:5'-ggaaagccagtccccagaac-3')
9.1 μL water "×2 Master Mix" and "Reference Dye" are contained in a real-time PCR kit manufactured by QIAGEN (trade name: Brilliant (registered trademark) SYBR (registered trademark) Green QPCR Master Mix, Catalogue No. #600548).

A primer set consisting of primer GADPH/DNA-F and primer GADPH/DNA-R primer is a primer set for amplifying a part of GAPDH in the genomic DNA.

The sample in Example 6, the sample in Comparative Example 1, and the sample in Comparative Example 2 were used in the same manner as in Examination 1 to prepare reaction solutions respectively.

Using these reaction solutions, real-time PCR was conducted by Mx3005P manufactured by STRATAGENE. A thermal profile of the real-time PCR was as follows:
95° C., 10 minutes,
40 cycles of 95° C. for 30 seconds, 58° C. for 15 seconds, and 72° C. for 30 seconds In real-time PCR, the fluorescence intensity of a fluorescence dye (trade name: Brilliant (registered trademark) SYBR (registered trademark) Green, manufactured by QIAGEN) intercalated in the amplification product being a double-stranded DNA was measured.

Assuming that the amount of GAPDH in the sample not being treated with γATP-dependent deoxyribonuclease was 100, the percentage of GAPDH in the sample treated with γATP-dependent deoxyribonuclease (percentage (%) of remaining GAPDH) was determined. The results are shown in FIG. 7. FIG. 7 shows measurement results by real-time PCR in Examination 1. In FIG. 7A, bar 1 shows the sample in Comparative Example 1, and bar 2 shows the sample in Example 5. In FIG. 7B, bar 1 shows the sample in Comparative Example 2, and bar 2 shows the sample in Example 6.

As can be seen from the results in FIG. 7, GAPDH in the sample treated with SacI (bar 2 in FIG. 7(A)) is lower than GAPDH in the sample not treated with SacI (bar 2 in FIG. 7(B)). From this result, it was found that the DNA obtained from a cell of a subject can be treated with the endonuclease prior to treatment with the exonuclease in order to significantly reduce the amount of the remaining genomic DNA.

Experiment 1

10 μL buffer (×5 buffer (composition: 334 mM glycine-sodium hydroxide (pH 9.4), 150 mM magnesium chloride, 42 mM 2-mercaptoethanol, 2.5 mM γATP)), 1 μL of 10 U/μL γATP-dependent deoxyribonuclease solution (trade name: ATP-Dependent Deoxyribonuclease, Code No. ADD-101, manufactured by Toyobo Co., Ltd.), and 36 μL of nuclease-free purified water were added to 3 μL of (0.3 μg/μL) aqueous solution of the genomic DNA of KATOIII cells obtained in the same manner as in Manufacturing Example 1, to give 50 μL reaction mixture. This reaction mixture was incubated at 37° C. for 3 hours and then incubated at 75° C. for 10 minutes. The reaction mixture was purified through a spin column for nucleic acid purification (trade name: MicroSpin S-300 HR Column, manufactured by GE Healthcare) to give the sample in Experiment 1.

Experiment 2

10 µL of the buffer used in Experiment 1, 1 µL of 10 U/µL γATP-dependent deoxyribonuclease solution, and 35 µL of nuclease-free purified water were added to 3 µL of (0.3 µg/µL) aqueous solution of the genomic DNA of KATOIII cells obtained in the same manner as in Manufacturing Example 1, to give a reaction mixture. This reaction mixture was incubated at 37° C. for 1 hour. 1 µL of 10 U/µL γATP-dependent deoxyribonuclease solution was further added thereto, and the mixture was incubated for 2 hours and then incubated at 75° C. for 10 minutes. The reaction mixture was purified through a spin column for nucleic acid purification (trade name: MicroSpin S-300 HR Column, manufactured by GE Healthcare) to give the sample in Experiment 2.

Experiment 3

10 µL of the buffer used in Experiment 1, 2 µL of 10 U/µL γATP-dependent deoxyribonuclease solution, and 35 µL of nuclease-free purified water were added to 3 µL of (0.3 µg/µL) aqueous solution of the genomic DNA of KATOIII cells obtained in the same manner as in Manufacturing Example 1, to give 50 µL reaction mixture. This reaction mixture was incubated at 37° C. for 3 hours and then incubated at 75° C. for 10 minutes. The reaction mixture was purified through a spin column for nucleic acid purification (trade name: MicroSpin S-300 HR Column, manufactured by GE Healthcare) to give the sample in Experiment 3.

Experiment 4

10 µL of the buffer used in Experiment 1, 1 µL of 10 U/µL γATP-dependent deoxyribonuclease solution, 2 µL of 10 U/µL SacI (manufactured by Takara Bio), and 34 µL of nuclease-free purified water were added to 3 µL of (0.3 µg/µL) aqueous solution of the genomic DNA of KATOIII cells obtained in the same manner as in Manufacturing Example 1, to give 50 µL reaction mixture. This reaction mixture was incubated at 37° C. for 3 hours and then incubated at 75° C. for 10 minutes. The reaction mixture was purified through a spin column for nucleic acid purification (trade name: MicroSpin S-300 HR Column, manufactured by GE Healthcare) to give the sample in Experiment 4.

Experiment 5

10 µL of the buffer used in Experiment 1, 1 µL of 10 U/µL γATP-dependent deoxyribonuclease solution, 2 µL of 10 U/µL XhoI (manufactured by Takara Bio), and 34 µL of nuclease-free purified water were added to 3 µL of (0.3 µg/µL) aqueous solution of the genomic DNA of KATOIII cells obtained in the same manner as in Manufacturing Example 1, to give 50 µL reaction mixture. This reaction mixture was incubated at 37° C. for 3 hours and then incubated at 75° C. for 10 minutes. The reaction mixture was purified through a spin column for nucleic acid purification (trade name: MicroSpin S-300 HR Column, manufactured by GE Healthcare) to give the sample in Experiment 5.

Experiment 6

10 µL of the buffer used in Experiment 1 and 37 µL of nuclease-free purified water were added to 3 µL of (0.3 µg/µL) aqueous solution of the genomic DNA of KATOIII cells, to give 50 µL reaction mixture. This reaction mixture was incubated at 37° C. for 3 hours and then incubated at 75° C. for 10 minutes. The reaction mixture was purified through a spin column for nucleic acid purification (trade name: MicroSpin S-300 HR Column, manufactured by GE Healthcare) to give the sample in Experiment 6.

Examination 2

The same operation was conducted as in Examination 1 except that the samples in Experiments 1 to 5 were used respectively in place of the sample in Example 5, the sample in Example 6, the sample in Comparative Example 1 or the sample in Comparative Example 2. Then, the fluorescence intensity based on a fluorescence dye (trade name: Brilliant (registered trademark) SYBR (registered trademark) Green, manufactured by QIAGEN) intercalated in the amplification product being a double-stranded DNA was measured.

Assuming that the amount of GAPDH in the sample in Experiment 6 was 100, the percentage of remaining GAPDH in each of the samples in Experiments 1 to 5 (percentage (%) of remaining GAPDH) was determined. The results are shown in FIG. 8. In the graph, bars 1 to 5 show the samples in Experiments 1 to 5, respectively.

From the results in FIG. 8, it can be seen that the percentage of GAPDH remaining in the sample treated with SacI or XhoI and with γATP-dependent deoxyribonuclease is lower than the percentage of GAPDH remaining in the sample treated with only γATP-dependent deoxyribonuclease. From this result, it was found that when the DNA obtained from a cell of a subject is treated with an enzyme having an endonuclease activity and an enzyme having an exonuclease activity simultaneously, the amount of the remaining genomic DNA can be significantly reduced.

From the results in Examinations 1 and 2, it was suggested that in the judgment method of the present invention, the DNA extracted from a cell of a subject is treated with an exonuclease and endonuclease to give a second sample, whereby the presence or absence of the integrated HPV in the cell can be measured rapidly and easily with high accuracy.

Experiment 7

An aqueous solution of the genomic DNA (3 µg) of KATOIII cells obtained by the same operation as in Manufacturing Example 1 was treated under the conditions in Table 1, with γATP-dependent deoxyribonuclease (trade name: ATP-Dependent Deoxyribonuclease, code number: ADD-101, manufactured by Toyobo Co., Ltd.), exonuclease (trade name: RingMaster (trademark) Nuclease, manufactured by Novagen), exonuclease III (manufactured by New England Bio Laboratory), T7 exonuclease (manufactured by New England Bio Laboratory) or lambda-exonuclease (manufactured by New England Bio Laboratory).

TABLE 1

| Enzyme | T7 exonuclease | ATP-dependent deoxyribonuclease | Lambda-Exonuclease | Exonuclease III | Ring Master (trademark) Nuclease |
|---|---|---|---|---|---|
| Buffer | Buffer Composition 50 mM potassium acetate 20 mM Tris-acetic acid 1 mM dithiothreitol (PH 7.9) | Buffer Composition 66.8 mM glycine-sodium hydroxide 30 mM magnesium chloride 8.4 mM 2-mercaptoethanol 0.5 mM γATP (PH 9.4) | Buffer Composition 67 mM glycine-potassium hydroxide 2.5 mM magnesium chloride 50 µg/ml BSA (PH 9.4) | Buffer Composition 10 mM bis-trispropane-sodium chloride 10 mM magnesium chloride 1 mM dithiothreitol (PH 7.0) | Ring Master Nuclease Buffer (manufactured by Novagen) |
| Amount of the enzyme | | 10U | | | 100U |
| Reaction conditions | 25° C. 0 h, 7 h | | 37° C., 0 h or 7 h | | |
| Inactivation | — | | 75° C. 20 minutes | | |

Each sample was subjected to agarose gel electrophoresis. The concentration of agarose in the gel used was 0.5% by mass. A photograph of the gel after electrophoresis is shown in FIG. 9. FIG. 9 is a photograph showing an electrophoresis pattern of samples obtained by treatment with various exonucleases in Experiment 7. In the photograph, lane 1 shows the sample treated with γATP-dependent deoxyribonuclease; lane 2, the sample treated with an exonuclease (trade name: RingMaster (trademark) Nuclease, manufactured by Novagen); lane 3, the sample treated with exonuclease III; lane 4, the sample treated with T7 exonuclease; and lane 5, the sample treated with lambda-exonuclease. FIG. 9(A) shows an electrophoresis pattern in the enzyme reaction for 0 hour, and FIG. 9(B) shows an electrophoresis pattern in the enzyme reaction for 7 hours.

In the case of the enzyme reaction time of 0 hour, a band showing strong fluorescence was observed in any lane. This indicates that the genomic DNA was electrophoresed before decomposition with the enzyme. On the other hand, when the enzyme reaction was conducted for 7 hours, fluorescence was hardly observed in any lane. This indicates that the genomic DNA was decomposed with the enzyme used in the experiment.

From the foregoing, it was found that any types of exonucleases used in the experiment, similar to γATP-dependent deoxyribonuclease, can be used in the method of detecting the integrated HPV DNA in this embodiment.

What is claimed is:

1. A method for detecting integrated HPV DNA, comprising:
   obtaining a first sample comprising DNA derived from a cell of a subject;
   obtaining a second sample comprising DNA derived from the cell, wherein the DNA in the second sample is treated with an enzyme which has exonuclease activity;
   obtaining a first information related to an amount of HPV DNA in the first sample, wherein the first information comprises information related to an amount of both episomal HPV DNA and integrated HPV DNA;
   obtaining a second information related to amount of an HPV DNA in the second sample, wherein the second information comprises information related to an amount of episomal HPV DNA, and does not substantially comprise information related to an amount of integrated HPV DNA; and
   detecting the integrated HPV DNA in the cell based on the first and second information;
   wherein the detecting is performed by determining that the integrated HPV DNA is contained in the cell if the total amount of HPV DNA in the first sample is larger than the total amount of HPV DNA in the second sample.

2. The method according to claim 1, further comprising determining whether HPV DNA is contained in the cell, based on the first and second information.

3. The method according to claim 1, wherein the first information is obtained by amplifying DNA in the first sample with a specific primer for amplifying HPV DNA.

4. The method according to claim 1, wherein the second information is obtained by amplifying DNA in the second sample with a specific primer for amplifying HPV DNA.

5. The method according to claim 3, wherein the DNA is amplified by polymerase chain reaction, strand displacement amplification, or ligase chain reaction.

6. The method according to claim 3, wherein the primer can be used to amplify a region selected from the group consisting of a E6 gene region, E7 gene region, L1 gene region, and L2 gene region.

7. The method according to claim 1, wherein the cell is derived from a uterine cervix or a oropharynx.

8. The method according to claim 1, wherein the HPV is a high-risk type of HPV.

9. The method according to claim 1, wherein the enzyme is at least one selected from the group consisting of ATP-dependent deoxyribonuclease, exonuclease III, T7 exonuclease, lambda-exonuclease, and Pfu DNA polymerase.

10. The method according to claim 1, further comprising:
    obtaining a third information related to the presence of a control gene of the cell in the first sample, wherein the control gene exists in a human genome and does not exist in a HPV genome; and
    determining the steps of the obtaining the first sample, the obtaining the second sample, the obtaining the first information, and the obtaining the second information are not appropriately performed, if the gene is not detected in the first sample and/or if the gene is detected in the second sample.

11. The method according to claim 10, wherein the control gene is a housekeeping gene.

12. The method according to claim 1, wherein the DNA in the second sample is treated with a second enzyme which has endonuclease activity not degrading HPV DNA.

13. The method according to claim 12, wherein the second enzyme is selected from the group consisting of ClaI, EcoRV, HindIII, NheI, NotI, Sad, SacII, SalI, SmaI, XbaI, and XhoI.

14. The method according to claim 12, wherein the DNA in the second sample is subsequently treated with a third enzyme having exonuclease activity.

15. A method for determining the presence or absence of integrated HPV DNA in a cell of a subject, comprising:
    obtaining a first sample comprising DNA derived from the cell;
    obtaining a second sample comprising DNA derived from the cell, wherein the DNA in the second sample is treated with an enzyme which has exonuclease activity;
    obtaining a first information related to an amount of HPV DNA in the first sample, wherein the first information comprises information related to an amount of both episomal HPV DNA and integrated HPV DNA;
    obtaining a second information related to an amount of HPV DNA in the second sample, wherein the second information comprises information related to an amount of episomal HPV DNA, and does not substantially comprise information related to an amount of integrated HPV DNA; and
    determining the presence or absence of the integrated HPV DNA in the cell based on the first and second information, wherein the determining is performed when the total amount of HPV DNA in the first sample is larger than the total amount of HPV DNA in the second sample.

16. A method for determining the presence or absence of integrated HPV DNA in a cell of a subject, comprising:
  obtaining a first information related to the amount of episomal and integrated HPV DNA in a first sample which comprises DNA derived from the cell;
  obtaining a second information related to the amount of episomal HPV DNA in a second sample which comprises DNA derived from the cell, wherein the DNA in the second sample is treated with an enzyme which has exonuclease activity; and
  determining the presence or absence of the integrated HPV DNA in the cell based on the first and second information;
  wherein the determining is performed by determining that the integrated HPV DNA is present in the cell if the amount of total HPV DNA in the first sample is larger than the total amount of HPV DNA in the second sample.

* * * * *

SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 1
tgctccatct gccactacgt c                                           21

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
tagggcgcaa ccacataaca                                             20

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 3
tgcatggaga tacacctaca ttg                                         23

```
<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 4
tagtgtgccc attaacaggt cttc                                          24

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 5
cgtccmarrg gawactgatc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 6
gcmcagggwc ataayaatgg                                               20

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 7
tttgttactg tggtagatac tac                                           23

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 8
gaaaaataaa ctgtaaatca tattc                                         25

<210> SEQ ID NO 9
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 9
caagacattg tattgcattt agagcc                                        26

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 10
```

```
tgctggaatg ctcgaaggtc                                               20

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 11
gtaggtgttg aggtaggtcg tgg                                           23

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 12
ggacaatcac ctggatttac tgc                                           23

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 13
tgtcaaaaac cgttgtgtcc                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 14
gagctgtcgc ttaattgctc                                               20

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 15
ggcaccctat ggacacgc                                                 18

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 16
ggaaagccag tccccagaac                                               20

<210> SEQ ID NO 17
<211> LENGTH: 18
<212> TYPE: DNA
<213> ORGANISM: Artificial Sequence
```

-continued

```
<220> FEATURE:
<223> OTHER INFORMATION: Synthetic oligonucleotide primer

<400> SEQUENCE: 17
ggcaccctat ggacacgc                                              18

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 18
ggaaagccag tccccagaac                                            20
```